United States Patent [19]

Berntsson et al.

[11] 4,035,420
[45] July 12, 1977

[54] SUBSTITUTED UREIDO ALKYLENE PHENOXY PROPANOLAMINES

[75] Inventors: Peder Bernhard Berntsson, Vastra Frolunda; Arne Elof Brändström, Goteborg N; Enar Ingemar Carlsson, Kungsbacka; Stig Ake Ingemar Carlsson, Molnlycke; Lars Ek, Kungsbacka; Gustav Benny Roger Samuelsson, Pixbo; Sven Erik Sjostrand, Kungsbacka; Gert Christer Strandlund, Molndal; Bengt Arne Hjalmar Ablad, Goteborg C, all of Sweden

[73] Assignee: Aktiebolaget Hassle, Molndal, Sweden

[21] Appl. No.: 618,754

[22] Filed: Oct. 2, 1975

Related U.S. Application Data

[62] Division of Ser. No. 376,947, July 6, 1973, Pat. No. 3,930,016.

[30] Foreign Application Priority Data

July 6, 1972 Sweden ........................... 8927/72

[51] Int. Cl.$^2$ ............... C07C 127/17; A61K 31/17
[52] U.S. Cl. .................... 260/553 A; 260/343.7; 260/459 R; 260/482 C; 260/501.17; 260/501.19; 260/553 R; 424/300; 424/316; 424/322
[58] Field of Search .... 260/553 A, 501.17, 501.19, 260/343.7, 459, 553 R, 329, 420

[56] References Cited

U.S. PATENT DOCUMENTS

| 3,562,297 | 2/1971 | Howe et al. ............... 260/562 A X |
|---|---|---|
| 3,644,520 | 2/1972 | Hartley et al. ............. 260/553 A X |
| 3,689,524 | 9/1972 | Jack et al. ................. 260/553 A X |
| 3,755,413 | 8/1973 | Köppe et al. ............. 260/562 A X |
| 3,845,123 | 10/1974 | Cox et al. ................. 260/553 A X |
| 3,925,446 | 12/1975 | Köppe et al. ................ 424/300 X |
| 3,928,601 | 12/1975 | Brandstrom et al. ............. 424/300 |
| 3,935,259 | 1/1976 | Wilhelm ....................... 260/553 A |

FOREIGN PATENT DOCUMENTS

| 292,671 | 9/1971 | Austria |
|---|---|---|
| 2,106,816 | 8/1971 | Germany |
| 1,260,893 | 1/1972 | United Kingdom |

OTHER PUBLICATIONS

Smith et al., CA 78:71716j (1973).
Smith, CA 80:27003s (1974).
Danilewicz et al., CA 74:99680j (1971).

*Primary Examiner* — Daniel E. Wyman
*Assistant Examiner* — Thomas A. Waltz
*Attorney, Agent, or Firm* — Brumbaugh, Graves, Donohue & Raymond

[57] ABSTRACT

New amines of the formula

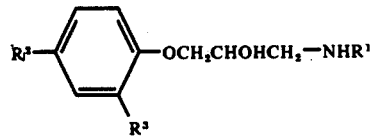

wherein the radicals $R^1$, $R^2$ and $R^3$ may be any of a variety of groups described below, several methods for preparing them and the use thereof in the treatment of cardiovascular diseases, particularly in blocking cardial and vascular beta-receptors.

15 Claims, No Drawings

SUBSTITUTED UREIDO ALKYLENE PHENOXY PROPANOLAMINES

This application is a divisioned application filed pursuant to 35 U.S.C. sec. 120 and 121, and claims the benefit of the filing date of parent application No. 376,947 filed July 6, 1973, now U.S. Pat. No. 3,930,016.

The present invention relates to new amines of formula I

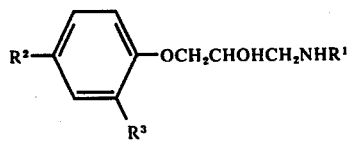

wherein $R^1$ is lower alkyl or hydroxy lower alkyl, $R^2$ is carbamoylamino lower alkyl, mono-lower alkyl carbamoylamino lower alkyl, di-lower alkyl carbamoylamino lower alkyl, carbamoylamino lower alkoxy, mono-lower alkyl carbamoylamino lower alkoxy, di-lower alkyl carbamoylamino lower alkoxy, carbamoyloxy lower alkyl, mono-lower alkyl carbamoyloxy lower alkyl, di-lower alkyl carbamoyloxy lower alkyl, carbamoyloxy lower alkoxy, mono-lower alkyl carbamoyloxy lower alkoxy or di-lower alkyl carbamoyloxy lower alkoxy, and $R^3$ is hydrogen, halogen, lower alkyl, lower alkenyl, lower alkinyl, lower alkoxymethyl lower alkoxy, lower alkenyloxy, lower alkinyloxy, lower alkylthio, lower alkenylthio, lower alkinylthio or lower acyl, and a process for their preparation.

As used herein, the term "lower" as applied to the type of substituent group, will be understood to mean groups having up to 7 carbon atoms, preferably up to 4 carbon atoms.

Lower alkyl $R^1$ has up to 7 carbon atoms and preferably up to 4 carbon atoms and is straight or branched especially branched at the α-carbon atom and is for example sec-butyl, or suitably tert.-butyl or preferably isopropyl.

Hydroxy lower alkyl $R^1$ has suitably up to 7 carbon atoms, preferably up to 4 carbon atoms and is straight or preferably branched, especially branched at the α-carbon atom and is e.g. 1-hydroxy-propyl-2 or 1-hydroxy-2-methyl-propyl-2.

Carbamoylamino lower alkyl, carbamoylamino lower alkoxy, carbamoyloxy lower alkyl and carbamoyloxy lower alkoxy $R^2$ has in each lower-alkyl part and lower alkoxy part up to 7 carbon atoms, preferably up to 4 carbon atoms and is straight or branched and is preferably propyl, ethyl or methyl, and propoxy, ethoxy or methoxy, respectively.

Each lower alkyl part of the lower alkyl carbamoylamino parts and lower alkyl carbamoyloxy parts has suitably up to 7 carbon atoms, preferably up to 4 carbon atoms and is straight or branched and is preferably isopropyl, n-propyl, ethyl or methyl.

The lower alkyl part and the lower alkoxy part which carries the lower alkyl carbamoylamino part and the lower alkyl carbamoyloxy part of the residue $R^2$ has suitably the same meaning as for the carbamoylamino lower alkyl, the carbamoylamino lower alkoxy, the carbamoyloxy lower alkyl and carbamoyloxy lower alkoxy and is e.g. propyl, ethyl, methyl, and propoxy, ethoxy, methoxy, respectively.

Halogen $R^3$ is e.g. fluoro, bromo and preferably chloro.

Lower alkyl $R^3$ has suitably up tp 7 carbon atoms, preferably up to 4 carbon atoms, as iso- and n-propyl, straight or branched chain and in any position bonded butyl, pentyl, hexyl and heptyl, suitably ethyl and preferably methyl.

Lower alkenyl $R^3$ has for example up to 7 carbon atoms, preferably 2 to 4 carbon atoms, as vinyl, 2-methylvinyl, methallyl and preferably allyl.

Lower alkinyl $R^3$ has for example up to 7 carbon atoms, preferably 2 to 4 carbon atoms as 1-propinyl, 2-propinyl and ethinyl.

Lower alkoxy methyl $R^3$ has in its lower alkyl part of the lower alkoxy, suitably up to 7 carbon atoms, preferably up to 4 carbon atoms as ethyl, iso- or n-propyl, and preferably methyl, and is e.g. ethoxy methyl and preferably methoxy methyl.

Lower alkoxy $R^3$ has suitably up to 7 carbon atoms, preferably up to 4 carbon atoms, and is e.g. ethoxy, iso- or n-propoxy, and preferably methoxy.

Lower alkenyloxy $R^3$ has e.g. up to 7 carbon atoms, preferably up to 4 carbon atoms as methallyloxy, or preferably allyloxy.

Lower alkinyloxy $R^3$ has e.g. up to 7 carbon atoms, preferably up to 4 carbon atoms as 2-propinyloxy.

Lower alkylthio $R^3$ has suitably up to 7 carbon atoms, preferably up to 4 carbon atoms, as methylthio, ethylthio, n-propylthio, isopropylthio, butylthio, pentylthio, especially methylthio and ethylthio.

Lower alkenylthio $R^3$ has suitably up to 7 carbon atoms, preferably 2 to 4 carbon atoms, as vinylthio, 2-methyl vinylthio, methallylthio and especially allylthio.

Lower alkinylthio $R^3$ has suitably up to 7 carbon atoms, preferably 2 to 4 carbon atoms, as ethinylthio, 1-propinylthio, 2-propinylthio.

Lower acyl $R^3$ has suitably up to 7 carbon atoms, preferably up to 4 carbon atoms, as formyl, acetyl, and propionyl.

The lower alkyl carbamoyl residues are mono-lower alkyl carbamoyl residues as well as di-lower alkyl carbamoyl residues, if not especially noted.

The new compounds have valuable pharmacological properties. Thus, they block cardial β-receptors, which is shown in the determination of the antagonism to tachycardia after an intravenous injection of 0.5 μg/kg of d/l-isoproterenol sulphate on an anaesthetized cat with an intravenous dose of 0.0002 to 2 mg/kg. Thus, they block the vascular β-receptors, which is shown by the determination of the antagonism to vasodilation after an intravenous injection of 0.5 μg/kg of d/l-isoproterenol sulphate on an anaesthetized cat with an intravenous dose of 3 mg/kg or more. Thus, they block the cardial β-receptors, which is shown in the determination of tachycardy after the addition of 0.005 μg/ml of d/-l-isoproterenol sulphate to an isolated guinea-pig heart in vitro at a concentration of 0.02 to 2 mg/ml.

The new compounds can be used as cardioselective antagonists of adrenergic β-receptor-stimulators e.g. in the treatment of arrhythmias and angina pectoris. One may also use them as valuable intermediates in the preparation of other useful compounds, especially pharmaceutically active compounds.

Outstanding amines are those according to formula Ia

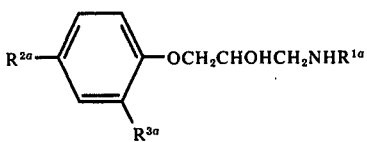

wherein $R^{1a}$ is lower alkyl having 1 to 4 carbon atoms or hydroxy lower alkyl having 1 to 4 carbon atoms, $R^{2a}$ is lower alkyl carbamoyloxy lower alkyl having up to 10 carbon atoms, and $R^{3a}$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms or lower alkenyloxy having 3 or 4 carbon atoms.

Of the compounds of the formula Ia such compounds are especially advantageous, when $R^{1a}$ is tert.-butyl, or isopropyl, 1-hydroxy propyl-2 or 1-hydroxy-2-methyl-propyl-2, $R^{2a}$ is methyl carbamoyloxy methyl, methyl carbamoyloxy ethyl, methyl carbamoyloxy propyl, di-methyl carbamoyloxy propyl or diethyl carbamoyloxy ethyl and $R^{3a}$ is hydrogen, chloro, bromo, methyl, allyl, methoxy methyl, methoxy or allyloxy.

Most preferred are those compounds according to formula Ia, wherein $R^{1a}$ is tert.-butyl or isopropyl, $R^{2a}$ is methyl carbamoyloxy propyl or di-ethyl carbamoyloxy ethyl and $R^{3a}$ is hydrogen, chloro, bromo, methyl, allyl, methoxy methyl, methoxy or allyloxy.

Outstanding amines are also those according to formula Ib

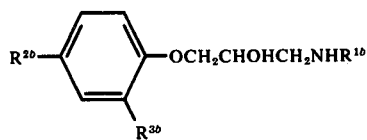

wherein $R^{1b}$ is lower alkyl having 1 to 4 carbon atoms, or hydroxy lower alkyl having 1 to 4 carbon atoms, $R^{2b}$ is lower alkyl carbamoyloxy lower alkoxy having up to 10 carbon atoms, and $R^{3b}$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, lower alkenyloxy having 3 or 4 carbon atoms.

Of the compounds of formula Ib such compounds are especially advantageous, wherein $R^{1b}$ is tert.-butyl, or isopropyl, 1-hydroxy propyl-2, or 1-hydroxy-2-methyl propyl-2, $R^{2b}$ is methyl carbamoyloxy ethoxy di-methyl carbamoyloxy ethoxy, ethyl carbamoyloxy ethoxy, ethyl cabamoyloxy ethoxy or diethyl carbamoyloxy ethoxy and $R^{3b}$ is hydrogen, chloro, bromo, methyl, allyl, methoxy methyl, methoxy or allyloxy.

Most preferred are those compounds according to formula Ib, wherein $R^{1b}$ is tert.-butyl, or isopropyl, $R^{2b}$ is hydrogen, chloro, bromo, methyl, allyl, methoxy methyl, methoxy or allyloxy.

Outstanding amines are also those according to formula Ic

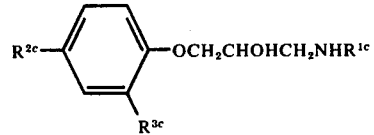

wherein $R^{1c}$ is lower alkyl having 1 to 4 carbon atoms, or hydroxy lower alkyl having 1 to 4 carbon atoms, $R^{2c}$ is lower alkyl carbamoylamino lower alkyl having up to 10 carbon atoms and $R^{3c}$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, or lower alkenyloxy having 3 or 4 carbon atoms.

Of the compounds of formula Ic such compounds are especially advantageous, wherein $R^{1c}$ is tert.-butyl, isopropyl, 1-hydroxy propyl-2 or 1-hydroxy-2-methyl propyl-2, $R^{2c}$ is methyl carbamoylamino methyl, methyl carbamoylamino ethyl, methyl carbamoylamino-n-propyl or di-methyl carbamoylamino ethyl and $R^{3c}$ is hydrogen, chloro, bromo, methyl, allyl, methoxy methyl, methoxy or allyloxy.

Most prefered are those compounds according to formula Ic, wherein $R^{1c}$ is tert.-butyl or isopropyl, $R^{2c}$ is di-methyl carbamoylamino ethyl or methyl carbamoylamino ethyl and $R^{3c}$ is hydrogen, chloro, bromo, methyl, allyl, methoxy methyl, methoxy or allyloxy.

Oustanding amines are also those according to formula Id

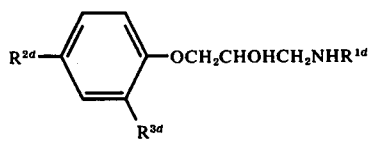

wherein $R^{1d}$ is lower alkyl having 1 to 4 carbon atoms, or hydroxy lower alkyl having 1 to 4 carbon atoms, $R^{2d}$ is carbamoylamino lower alkyl having up to 5 carbon atoms, and $R^{3d}$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, lower alkenyloxy having 3 or 4 carbon atoms.

Of the compounds of formula Id such compounds are especially advantageous, wherein $R^{1d}$ is tert.-butyl, isopropyl, 1-hydroxy propyl-2, or 1-hydroxy-2-methyl propyl-2, $R^{2d}$ is carbamoylamino methyl, carbamoylamino ethyl, carbamoylamino-n-propyl, carbamoylamino-n-butyl and $R^{3d}$ is hydrogen, chloro, bromo, methyl, allyl, methoxy methyl, methoxy or allyloxy.

Most preferred are those compounds according to formula Id, wherein $R^{1d}$ is tert.-butyl or isopropyl, $R^{2d}$ is carbamoylamino ethyl or carbamoylamino propyl and $R^{3d}$ is hydrogen, chloro, bromo, methyl, allyl, methoxy methyl, methoxy or allyloxy.

Outstanding amines are also those according to formula Ie

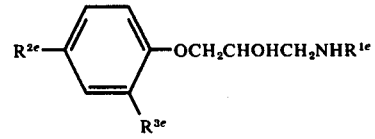

wherein $R^{1e}$ is lower alkyl having 1 to 4 carbon atoms, or hydroxy lower alkyl havin 1 to 4 carbon atoms, $R^{2e}$ is carbamoyloxy lower alkyl having up to 5 carbon atoms, and $R^{3e}$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, lower alkenyloxy having 3 or 4 carbon atoms.

Of the compounds of formula Ie such compounds are especially advantageous, wherein $R^{1e}$ is tert.-butyl, isopropyl, 1-hydroxy propyl-2, or 1-hydroxy-2-methyl propyl-2, $R^{2e}$ is carbamoyloxy methyl, carbamoyloxy ethyl or carbamoyloxy propyl and $R^{3e}$ is hydrogen, chloro, bromo, methyl, allyl, methoxy methyl, methoxy or allyloxy.

Most preferred are those compounds according to formula Ie wherein $R^{1e}$ is tert.-butyl or isopropyl, $R^{2e}$ is carbamoyloxy ethyl and $R^{3e}$ is hydrogen, chloro, bromo, methyl, allyl, methoxymethyl, methoxy or allyloxy.

Outstanding amines are also those according to formula if

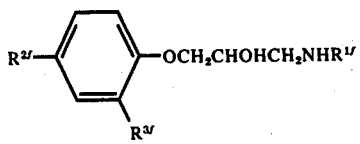

(If)

wherein $R^{1f}$ is lower alkyl having 1 to 4 carbon atoms or hydroxy lower alkyl having 1 to 4 carbon atoms, $R^{2f}$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, lower alkinyloxy having 3 or 4 carbon atoms.

Of the compounds of formula If such compounds are especially advantageous, wherein $R^{1f}$ is tert.-butyl, isopropyl, 1-hydroxy propyl-2, or 1-hydroxy-2-methyl propyl-2, $R^{2f}$ is carbamoyloxy methoxy, carbamoyloxy ethoxy, or carbamoyloxy-n-propoxy, and $R^{3f}$ is hydrogen, chloro, bromo, methyl, allyl methoxy methyl, methoxy or alloyloxy.

Most preferred are those compounds according to formula If wherein $R^{1f}$ is tert.-butyl or isopropyl, $R^{2f}$ is carbamoyloxy ethoxy and $R^{3f}$ is hydrogen, chloro, bromo, methyl, allyl, methoxy methyl, methoxy or allyloxy.

Outstanding amines are also those according to formula Ig

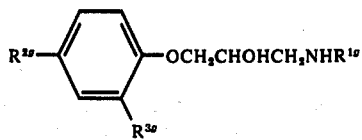

(Ig)

wherein $R^{1g}$ is lower alkyl having 1 to 4 carbon atoms, or hydroxy lower alkyl having 1 to 4 carbon atoms, $R^{2g}$ is carbamoylamino lower alkoxy having up to 5 carbon atoms, and $R^{3g}$ is hydrogen, halogen, lower alkyl having 1 to 4 atoms, lower alkenyl having 2 to 4 carbon atoms, lower alkoxy methyl having up to 5 carbon atoms, lower alkoxy having 1 to 4 carbon atoms, lower alkenyloxy having 3 or 4 carbon atoms.

Of the compounds of formula Ig such compounds are especially advantageous, wherein $R^{1g}$ is tert.-butyl, isopropyl, 1-hydroxy propyl-2, or 1-hydroxy-2-methyl propyl-2, $R^{2g}$ is carbamoylamino methoxy, carbamoylamino ethoxy or carbamoylamino-n-propoxy, and $R^{3g}$ is hydrogen, chloro, bromo, methyl, allyl, methoxymethyl, methoxy or allyloxy.

Most preferred are those compounds according to formula Ig wherein $R^{1g}$ is tert.-butyl or isopropyl, $R^{2g}$ is carbamoylamino ethoxy, and $R^{3g}$ is hydrogen, chloro, bromo, methyl, allyl, methoxy methyl, methoxy and allyloxy.

The following compounds are especially mentioned:

1. 1-[4-(2-methyl carbamoyloxy ethoxy)-phenoxy]-2-hydroxy-3-isopropylamino-propane,
2. 1-[2-chloro-4-(2-dimethyl carbamoyloxy ethoxy)-phenoxy]-2-hydroxy-3-isopropylamino-propane,
3. 1-[4-(2-carbamoyloxy ethoxy)-phenoxy]-2-hydroxy-3-isopropylamino-propane,
4. 1-[4-(3-methylcarbamoyloxy propyl)-phenoxy]-2-hydroxy-3-isopropylamino-propane;
5. 1-[4-(2-carbamoylamino ethyl)-phenoxy]-2-hydroxy-3-isopropylamino-propane,
6. 1-[4-(2-dimethylcarbamoylamino ethyl)-phenoxy]-2-hydroxy-3-isopropylamino-propane,
7 1-[2-chloro-4-(2-carbamoylamino ethyl)-phenoxyl]-2-hydroxy-3-isopropylamino-propane,
8. 1-[4-(4-(3-carbamoylaminopropyl)-phenoxy]-2-hydroxy-3-isopropylamino-propane,
9. 1-[4-(2-methylcarbamoylaminoethyl)-phenoxy]-2-hydroxy-3-isopropylamino-propane,
10. 1-[4-(2-carbamoyloxyethyl)-phenoxy]-2-hydroxy-3-isopropylamino-propane,
11. 1-[4-chloro-4-(2-methylcarbamoyloxyethyl)-phenoxy]-2-hydroxy-3-isopropylamino-propane,
12. 1-[4-(2-methylcarbamoyloxyethyl)-phenoxy]-2-hydroxy-3-isopropylamino-propane,
13. 1-[4-(2-dimethylcarbamoyloxyethyl)-phenoxy]-2-hydroxy-3-isopropylamino-propane, which block the cardial β-receptors, as is shown in the determination of the antagonism to tachycardia after an intravenous injection of 0.5 μg/kg of d/l-isoproterenol sulphate on an anaesthetized cat with an intravenous dose of 0.03 to 1 mg/kg, which block the vascular β-receptors as is shown in the determination of the antagonism to the vasodilation with an intravenous injection of 0.5 μg/kg of d/l-isoproterenol sulphate to the anaesthetized cat with an intravenous dose from 3 mg/kg or more, and which block the cardial β-receptors as is shown in the determination of the antagonism to tachycadia after an addition of 0.005 μg/ml of d/1-isoproterenol sulphate to an isolated guinea-pig heart in vitro at a concentration of 0.03 to 1 μg/ml.

The new compounds are obtained according to methods known per se. Thus a compound of formula II

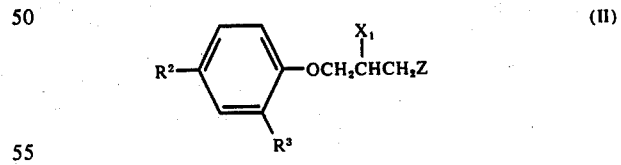

(II)

wherein $R^2$ and $R^3$ have the meeting given above, $X_1$ is a hydroxy group and Z is a reactive, esterified hydroxy group, or $X_1$ and Z together form an epoxy group, is reacted with an amine of the formula $NH_2-R^1$, wherein $R^1$ has the same meaning as given above.

A reactive, esterfied hydroxy group is particularly a hydroxy group esterified with a strong, inorganic or organic acid, preferably a hydrohalogen acid, as hydrochloric acid, hydrobromic acid, or hydroiodic acid, further sulphuric acid or a strong organic sulphonic acid as a strong aromatic sulphonic acid, e.g. benzenesulphonic acid, 4-bromobenzenesulphonic acid or 4- toluenesulphonic acid. Thus, Z is preferably chloro, bromo or iodo.

This reaction is carried out in a known way. When a reactive ester is used as a starting material the preparation takes place preferably in the presence of a basic condensing agent and/or with an excess of an amine. Suitable basic condensing agents are e.g. alkali metal hydroxides, such as sodium or potassium hydroxide, alkali metal carbonates such as potassium carbonate and alkali metal alcoholates such as sodium methylate, potassium ethylate or potassium tert.-butylate.

Further, a compound of formula III

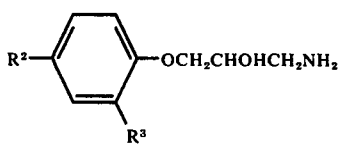
(III)

wherein $R^2$ and $R^3$ have the same meanings as given above, is reacted with a compound of the formula $Z-R^1$, wherein $R^1$ is Z have the same meanings as given above.

This reaction is carried out in a known way, preferably in the presence of a basic condensing agent and/or an excess of an amine. Suitable basic condensing agents are e.g. alkali alcoholates, preferably sodium or potassium alcoholate, or also alkali carbonates such as sodium or potassium carbonate.

Further, a compound of formula IV

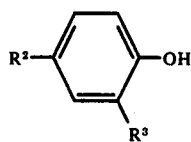
(IV)

wherein $R^2$ and $R^3$ have the same meanings as given above is reacted with a compound of formula V

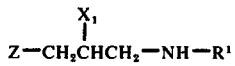
(V)

wherein Z, X and $R^1$ have the same meanings as given above.

This reaction is carried out in a known way. In those cases where reactive esters are used as starting material, the compound of formula IV may suitably be used in the form of its metal phenolate such as alkali metal phenolate, preferably sodium phenolate, or one may work in the presence of an acid binding agent, preferably a condensing agent, which can form a salt of the compound of formula IV, such as an alkali metal alcoholate.

Further, one may split off a residue from a compound of formula I above, wherein $R^1$, $R^2$ and $R^3$ have the same meanings as above and in which the nitrogen atom of the amino group and/or the hydroxy group has attached thereto a splitable residue.

Such splitable residues are especially those which are splitable by solvolysis, reduction, pyrolysis or fermentation.

Residues splitable by solvolysis are preferably residues splitable by hydrolysis or ammonolysis.

Residues splitable by means of hydrolysis are e.g. an acyl residue, which, when present are functionally varies carboxy groups, e.g. oxycarbonyl residues, such as alkoxycarbonyl residues, e.g. tert.-butoxycarbonyl residue, or ethoxycarbonyl residue, aralkoxycarbonyl residues such as phenyl lower alkoxy carbonyl residues, e.g. a carbobenzyloxy residue halogen carbonyl residue, e.g. a chlorocarbonyl residue, further arylsulphonyl residues such as toluene sulphonyl or bromobenzene sulphonyl residues, or halogenated, such as fluorinated lower alkanoyl residues, e.g. formyl-, acetyl- or tri-fluoroacetyl residue or a benzyl residue or cyano group or silyl residue, such as a trimethylsilyl residue.

Of the above-mentioned residues present on the hydroxy groups, which residues are splitable by hydrolysis, preferably the oxycarbonyl residues and the lower alkanoyl residues or the benzoyl residues are used.

Besides those mentioned above, also double-bonded residues, which are splitable at the amino group by hydrolysis are used, e.g. alkylidene or benzylidene residue or a phosphorylidene group such as a triphenylphosphorylidene group, whereby the nitrogen atom then obtains a positive charge.

Residues splitable at the hydroxy group and the amino group by hydrolysis are furthermore divalent residues such as occur in substituted methylene. As subtitutents on the methylene residues any organic residue may be used, so that it does not matter in the hydrolysis which compound is the substituent on the methylene residue. As methylene substitutents e.g. aliphatic or aromatic residue such as alkyl as mentioned above, aryl e.g. phenyl or pyridyl may be used. The hydrolysis may be carried out in any known way, suitably in a basic or preferably in an acid medium.

Compounds having residues which are splitable by hydrolysis are also the compounds according to formula VI

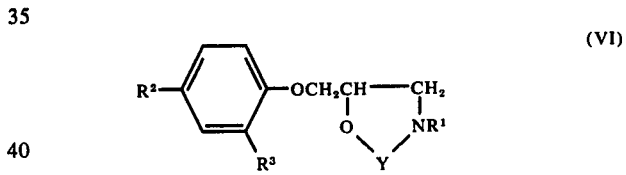
(VI)

wherein $R^1$, $R^2$ and $R^3$ have the same meanings as given above and Y is a carbonyl or thiocarbonyl residue.

The hydrolysis is carried out in a known way, e.g. in the presence of a hydrolyzing agent, e.g. in the presence of acidic agent as e.g. dilute mineral acids, such as sulphuric acid or hydrohalogen acid, or in the presence of basic agents as e.g. alkali metal hydroxides, such as sodium hydroxide. Oxycarbonyl residues, aryl sulphonyl residues and cyano groups may in a suitable manner be split off by means of acidic agents, such as a hydrohalogen acid, suitably hydrobromic acid. Preferably, the splitting may take place using dilute hydrobromic acid, suitably in a mixture with acetic acid. Cyano groups are preferably split off by means of hydrobromic acid at an elevated temperature, as in boiling hydrobromic acid, according to the "bromocyano method" (v. Braun). Further, e.g. a tert.-butyoxycarbonyl residue may be split off under anhydrous conditions by means of a treatment with a suitable acid, such as trifluoroacetic acid. Acidic agents are preferably used in the hydrolysis of compounds of formula VI.

Residues splitable by ammonolysis are especially the halogencarbonyl residues, such as the chlorocarbonyl residue. The ammonolysis may be carried out in a usual way, e.g. by means of an amine containing at least one hydrogen atom bonded to the nitrogen atom, such as a mono- or di-lower alkyl amine, e.g. methylamine or dimethylamine, or preferably ammonia, preferably at an elevated temperature. Instead of ammonia one may use an agent which gives ammonia such as hexamethylenetetraamine.

Residues splitable by means of a reduction are e.g. an α-arylalkyl residue, such as a benzyl residue or an α-aralkoxycarbonyl residue such as a benzyloxycarbonyl residue, which in a known way may be split off by hydrogenolysis, especially by catalytically activated hydrogen, e.g. by hydrogen in the presence of hydrogenating catalysts, e.g. Raney nickel. Further residues splitable by means of hydrogenolysis are 2-halogen alkoxycarbonyl residues, such as 2,2,2-trichloroethoxycarbonyl residues or 2-iodoethyoxy- or 2,2,2-tribromoethoxycarbonyl residues, which may be split off in a known way, suitably by metallic reduction (so-called nascent hydrogen). Nascent hydrogen may be obtained by the action of metal or metal alloys such as amalgam on compounds which give hydrogen, such as carboxy acids, alcohols or water. Zinc or zinc-alloys together with acetic acid may be used. Hydrogenolysis of 2-halogen alkoxycarbonyl residues may further take place using chromium or chromium (II) compounds, such as chromium (II) chloride or chromium (II) acetate.

A residue splitable by reduction may also be an aryl sulphonyl group such as a toluene sulphonyl group, which in a known way may be split off by reduction using nascent hydrogen, e.g. by means of an alkali metal, such as lithium or sodium in liquid ammonia, and suitably may be split off from a nitrogen atom. In carrying out the reduction, one has to provide that other reducing groups are not affected.

Residues splitable by means of pyrolysis, especially residues splitable from the nitrogen atom, may be substituted, or unsubstituted carbamoyl groups. Suitable substituents are e.g. lower alkyl, or aryl lower alkyl, such as methyl or benzyl or aryl, such as phenyl. The pyrolysis is carried out in a known way, but one may have to take care of the fact that other thermally susceptible groups are present, and avoid affecting them.

Residues splitable by means of fermentation, especially residues splitable from the nitrogen atom are in some cases substituted, however suitably unsubstituted carbamoyl groups may be present. Suitable substituents are e.g. lower alkyl or aryl lower alkyl, such as methyl or benzyl, or aryl, such as phenyl. The fermentation is carried out in a known way, e.g. by means of the enzyme urease or soybean extract at about 20° C or a slightly elevated temperature.

Further, a Schiff's base of formula VII or VII

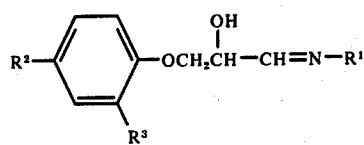
(VII)

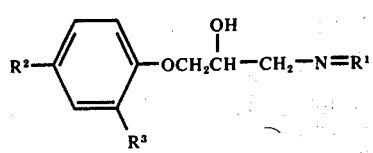
(VIII)

or a cyclic tautomer of formula IX corresponding to formula VIII

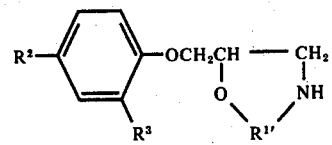
(IX)

can be reduced, wherein $R^1$, $R^2$ and $R^3$ have the same meaning as given above and $R^{1'}$ H is the same as $R^1$, so that the compounds of formula VIII and IX may exist together.

This reduction is carried out in a known way, e.g. using a di-light metal hydride, such as sodium boron hydride, lithium aluminium hydride, using a hydride such as Boran with formic acid, or by means of a catalytic hydrogenation, as with hydrogen in the presence of Raney nickel. During the reduction one has to take care that other groups are not affected.

Further, in a compound of formula XI

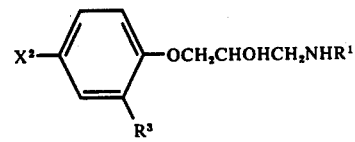
(XI)

wherein $R^1$ and $R^3$ have the same meanings a given above, and wherein $X^2$ is a residue which is able to be transformed to a residue $R^2$ having the same meaning as given above, one transforms $X^2$ to $R^2$.

A residue $X^2$ able to be transformed into $R^2$ is e.g. a residue $X^2$ transformable to a carbamoylamino lower alkyl, lower alkyl carbamoyl lower alkyl, carbamoyloxy lower alkyl or lower alkyl carbamoyloxy lower alkyl residue $R^2$, such as a $Z^1$-lower alkyl residue. A compound XI having such a residue $Z^1$-lower alkyl such as $X^2$ can be reacted in a known way with a compound carbamoyl-$Z^2$, or lower alkyl carbamoyl-$Z^2$ whereby one of $Z^1$ and $Z^2$ is a hydroxy group or mercapto group and the other being Z having the meaning given above. Thus, one can react either a compound of formula XII

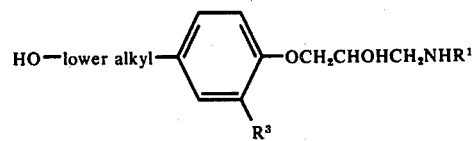
(XII)

with a compound carbamoyl-$Z^2$ or lower alkyl carbamoyl-$Z^2$; or a compound of formula XIII

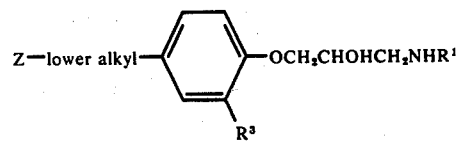
(XIII)

with carbamoylamine or a di-lower alkyl carbamoylamine wherein $R^1$, $R^3$ and Z have the same meanings as given above. The reaction is carried out in a known way, e.g. as the reaction of a compound of formula II with an amine $NH_2R^1$.

A residue $X^2$ transformable into $R^2$ is e.g. a residue $X^2$ tranformable into a carbamoylamino lower alkoxy, lower alkyl carbamoylamino lower alkoxy, carbamoyloxy lower alkoxy or lower alkyl carbamoyloxy lower alkoxy residue $R^2$, as a residue $Z^1$-lower alkyl-O- or a hydroxy group.

A compound XI with such a residue Z-lower alkyl-O- such as $X^2$ can be reacted in a known way with a carbamoyl-$Z^2$ or a lower alkyl carbamoyl-$Z^2$ wherein Z has the same meanings as given above. One of the residues $Z^1$ and $Z^2$ may be hydroxy or carbamoylamine or a lower alkyl carbamoylamine, the residue $Z^1$ being Z having the meaning given above.

Thus, one can either react a compound of formula XV

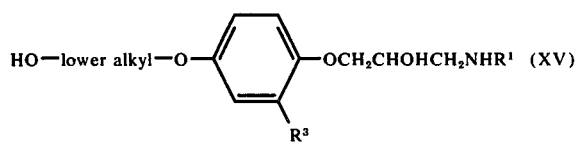

with a compound carbamoyl-$Z^2$ or lower alkyl carbamoyl-$Z^2$; or a compound of formula XVI

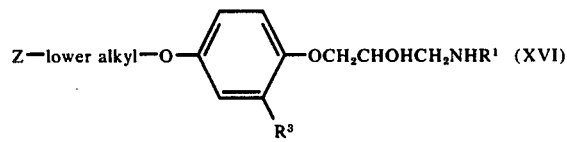

with carbamoylamine or a di-lower alkyl carbamoylamine; or a compound of the formula XVI above, with a compound di-lower alkyl carbamic acid, wherein $R^1$, $R^3$ and Z have the same meanings as given above. The reaction is carried out in a known way, e.g. as the reaction of a compound of formula II with an amine $NH_2$-$R^1$.

A compound of formula XI having a hydroxy group as a residue $X^2$ can be reacted in a known way with a compound carbamoylamino lower alkyl-Z, lower alkyl carbamoylamino lower alkyl-Z, carbamoyloxy lower alkyl-Z or lower alkyl carbamoyloxy lower alkyl-Z wherein Z has the same meaning as above.

Thus, one can react a compound of formula XVII

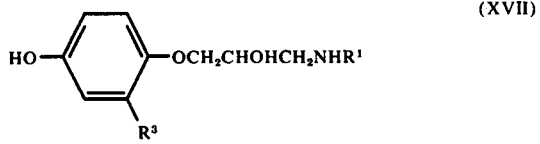

with a compound carbamoylamino lower alkyl-Z, lower alkyl carbamoyloxy lower alkyl-Z, or lower alkyl carbamoyl lower alkyl-Z, wherein $R^1$, $R^3$ and Z have the same meanings as given above. The reaction is carried out in a known way, e.g. as the reaction of a compound of formula II with an amine $NH_2$-$R^1$.

A residue $X^2$ transformable into $R^2$ is e.g. a residue $X^2$ transformable into a carbamoylamino lower alkyl or carbamoylamino lower alkoxy residue $R^2$, such as a residue $H_2N$-lower alkyl or a residue $H_2N$-lower alkoxy.

A compound XI having such a residue $H_2N$-lower alkyl- or $H_2N$-lower alkoxy such as $X_2$ can be reacted in a known way with a cyanate or carbamoyl chloride. Potassium, sodium or ammonium cyanate may be used.

Thus one can react a compound of the formula XVIII

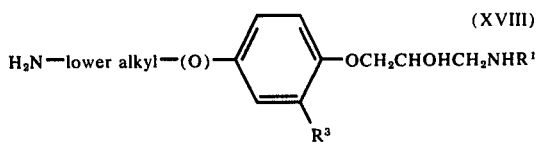

with a cyanate or carbamoyl chloride, wherein $R^1$ and $R^3$ have the meanings given above. The reaction is carried out in a known way e.g. as the reaction of a compound of the formula II with an amine $NH_2$-$R^1$.

A residue $X^2$ transformable into $R^2$ is e.g. a residue $X^2$ transformable into lower alkyl carbamoylamino lower alkyl or lower alkyl carbamoylamino lower alkoxy residue $R^2$, such as a residue $H_2N$ lower alkyl or a residue $H_2N$-lower alkoxy.

A compound XI having such a residue $H_2N$-lower alkyl or $H_2N$-lower alkoxy as $X^2$ can be reacted in a known way with a compound lower alkyl carbamoyl-Z, wherein Z has the meaning given above.

Thus one can react a compound of the formula XVIII with a compound lower alkyl carbamoyl-Z, wherein $R^1$, $R^3$ and Z have the meanings given above. The reaction is carried out in a known way e.g. as the reaction of a compound of the formula II with an amine $NH_2$-$R^1$.

In a known way the substituents may be varied from those exemplified. Furthermore, the compounds obtained may be introduced, split off or transformed into other end products in a known way.

Thus, it is possible to hydrogenate catalytically C-C double-bonds or C-C triple bonds to C-C single bonds by means of hydrogen in the presence of a hydrogenation catalyst, e.g. platinum, palladium or nickel, such as Raney nickel. One should, of course, provide that other reducible groups are not reduced.

In compounds obtained containing a C-C triple bond this may further be transformed into a C-C double bond and, if desired, be hydrogenated stereospecifically into a C-C-cis or C-C-trans double bond. The hydrogenation of a C-C triple bond to a C-C double bond may for example be carried out using 1 mole of hydrogen in the presence of a less active hydrogenation catalyst, such as iron or palladium, e.g. Raney iron or palladium with barium sulphate, preferably at an elevated temperature. The hyrogenation to a C-C-cis double bond may take place e.g. between 1 mole of hydrogen and a deactivated catalyst, such as palladium on active carbon and in the presence of quinoline, palladium on calcium carbonate in the presence of lead salts or Raney nickel. The hydrogenation to a C-C-trans double bond may take place by means of sodium in liquid ammonia, in which case with regard to other reducible groups short reaction times are used and no excess of the reducing agent is used. An ammonium halogenide, such as ammonium chloride, may be added as a catalyst.

In the reduction mentioned above one has to see to it that no further reducible groups are reduced. In the reduction using Raney nickel and hydrogen one has to consider especially the possibility of the presence of a halogen atom bonded to the aromatic ring, and provide that it is not replaced by hydrogen. Furthermore, in all reductions, especially catalytic hydrogenations, one has to consider any thioether group present. Preferably, sulphur resistant catalysts are used and, in actual cases, the volume of hydrogen to be absorbed is calculated and when the calculated amount is absorbed in the hydrogenation, the reduction is terminated.

The above-mentioned reactions may possibly be carried out simultaneously or sequentially in any sequence.

The above-mentioned reactions are carried out in a manner known per se in the presence or absence of diluting, condensing and/or catalytic agents at a low, room or an elevated temperature, suitably in a closed vessel.

Depending on the process conditions and the starting material, the end product is obtained either in free form or in the form of its acid addition salt, which is included in the scope of the invention. Thus, for example, basic, neutral or mixed salts may be obtained as well as hemiamino, sesqui- or polyhydrates. The acid addition salts of the new compounds may in manner known per se be transformed into free compounds using e.g. basic agents such as alkali or ion exchange. On the other hand, the free bases obtained may form salts with organic or inorganic salts. In the preparation of acid addition salts preferably such acids are used which form suitable therapeutically acceptable salts. Such acids are e.g. hydrohalogen acids, sulphuric acid, phosphoric acid, nitric acid, perchloric acid, aliphatic, alicyclic, aromatic or heterocyclic carboxy or sulphonic acids, such as formic, acetic, propionic, succinic, glycolic, latic, malic, tartaric, citric, ascorbic, maleic, hydroxy maleic or pyruvic acid, phenyl acetic, benzoic, p-aminobenzoic, anthranilic, p-hydroxybenzoic salicyclic or p-aminosalicyclic acid, embonic acid, methanesulphonic, ethanesulphonic hydroxyethane sulphonic, ethylene sulphonic acids, halogen benzene sulphonic, toluene sulphonic, naphthyl sulphonic acids or sulphanilic acid, Methionine, tryptophane, lysine or arginine.

These or other salts of the new compounds as e.g. picrates may serve as purifying agents of the free bases obtained. As the free bases are transformed into salts, there are separated and the bases are then set free from the salts again. According to the close relationship between the new compounds in free form and in the form of their salts it will be understood from the above and the following that, if possible, the corresponding salts are included herein.

The invention also relates to any embodiment of the process by which one starts from any compound obtained as an intermediate in any process step and one carries out the other process step, or one breaks off the process at any step, or in which one forms a starting material under the reaction conditions, or in which a reaction component possibly in the form of its salt is present.

Thus, one may react an aldehyde of the formula XIX

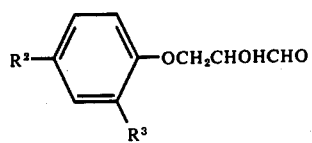

(XIX)

wherein $R^2$ and $R^3$ have the same meaning as given above, with an amine of the formula $H_2N\text{-}R^1$, wherein $R^1$ has the same meaning as given above, in the presence of a suitable reducing agent, such as one of those mentioned above. Thereby, a compound of formula VII is obtained as an intermediate, which then is reduced according to the invention.

Further, one may in a manner known per se react an amine of the formula III with an aldehyde or a ketone of the formula $O=R^1$, wherein $R^1$ has the above meaning in the presence of a suitable reducing agent, as one of those mentioned above. Thereby, a compound of formula VIII or IX is obtained as an intermediate, which then is reduced according to the invention.

Other compounds of the formula IX, which can be used are those wherein

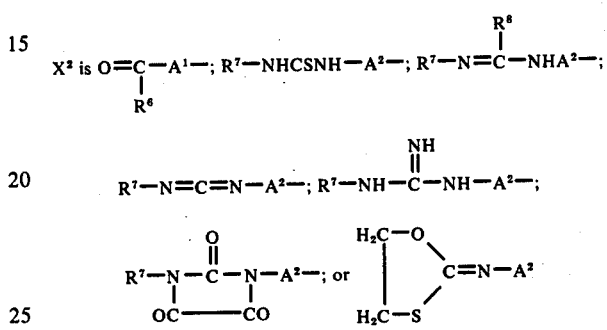

wherein $A^1$ is -NH-lower alkyl-, -NH-lower alkoxy-, -O-lower alkyl or -O-lower alkoxy-, $A^2$ is -lower alkyl or -lower alkoxy-, $R^6$ is alkoxy having 1 to 4 carbon atoms, possibly substituted phenoxy, alkylthio having 1 to 4 carbon atoms, possibly substituted phenylthio, hydrazino, halogen, or together with NH a further C-N-bond, $R^7$ is hydrogen or lower alkyl and $R^8$ is halogen, an O-acyl group, S-acyl group or a S-alkyl group.

Thus a compound of the formula 1

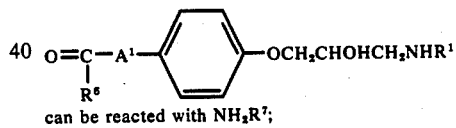

i)

can be reacted with $NH_2R^7$;

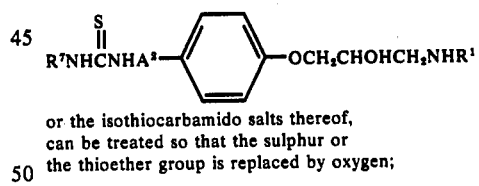

ii)

or the isothiocarbamido salts thereof, can be treated so that the sulphur or the thioether group is replaced by oxygen;

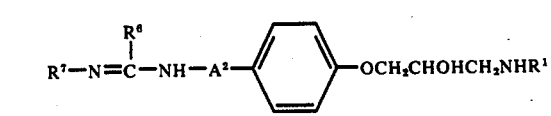

iii)

can be hydrolyzed;

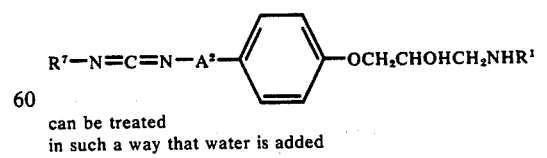

iv)

can be treated
in such a way that water is added

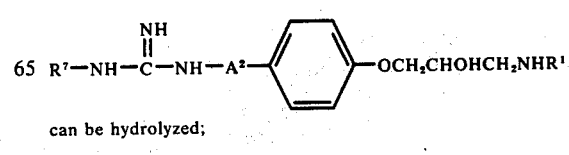

v)

can be hydrolyzed;

-continued

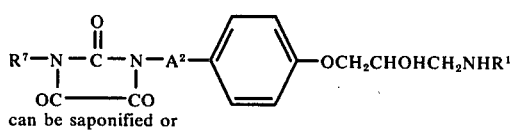

can be saponified or

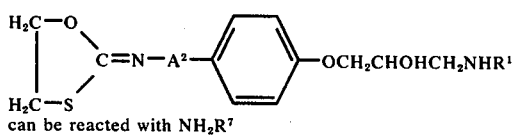

can be reacted with $NH_2R^7$

Further one can hydrogenate a compound of the formula XX

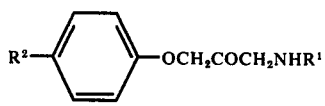

(XX)

The new compounds may, depending on the choice of starting materials and process, be present as optical antipodes or racemate, or if they contain at least two asymmetric carbon atoms, be present as an isomer mixture (racemate mixture).

The isomer mixtures (racemate mixtures) obtained may, depending on physical-chemical differences of the components, be separated into both stereoisomeric (diastereomeric) pure racemates, e.g. by means of chromatography and/or fractional crystallization.

The racemates obtained can be separated according to known methods, e.g. by means of recrystallization from an optically active solvent, by means of microorganisms, or by a reaction with optically active acids forming salts of the compound and separating the salts thus obtained, e.g. by means of their different solubility of the disastereomers, from which the antipodes by the influence of a suitable agent may be set free. Suitable optically active acids are e.g. the L- and D-forms of tartaric acid, di-o-tolyl-tartaric acid, maleic acid, mandelic acid, camphor sulphonic acid or china acid. Preferably, the more active part of the two antipodes is isolated.

Suitably such starting materials are used for carrying out the reactions of the invention, which lead to end products primarily desired.

The starting materials are known or may, if they should be new, be obtained according to processes known per se.

In clinical use the compounds of the invention are normally administered orally, rectally or by injection in the form of a pharmaceutical preparation, which contains an active component either as free base or as pharmaceutically acceptable, non-toxic acid addition salt, as e.g., the hydrochloride, lactate, acetate, sulphamate or the like in combination with a pharmaceutically acceptable carrier. Mention of the new compounds of the invention is intended to include either the free amine base or the acid addition salts of the free base, provided that the context in which such expressions are used permits. The carrier may be a solid, semisolid or liquid diluent or a capsule. These pharmaceutical preparations are a further embodiment of the invention. Usually the amount of active compound is between 0.1 to 99% by weight preferably 0.1 to 95% by weight of the preparation, suitably between 0.5 to 20% by weight in preparations for injection and between 0.2 to 50% by weight in preparations for oral administration.

In the preparation of pharmaceutical preparations containing a compound of the present invention in the form of dosage units for oral administration the compound elected may be mixed with a solid, pulverulent carrier, as e.g. with lactose, saccharose, sorbitol, mannitol, starch, as potato starch, corn starch amylopectin, cellulose derivatives or gelatine, as well as with a lubricant such as magnesium stearate, calcium stearate, polyethyleneglycol waxed or the like, and be pressed into tablets. If coated tablets are desired, the above prepared core may be coated with concentrated solution of sugar, which solution may contain, e.g. gum arabicum, gelatine, talc, titanium dioxide or the like. Furthermore, the tablets may be coated with a lacquer dissolved in an easily volatile organic solvent or mixture of solvents. To this coating a dye may be added in order to easily distinguish between tablets with different active compounds or with different amounts of the active compound present.

In the preparation of soft gelatin capsules (pearl-shaped, closed capsules), which consist of gelatin, and e.g. glycerine or in the preparation of similar closed capsules the active compound is mixed with a vegetable oil. Hard gelatin capsules may contain granules of the active compound in combination with a solid, pulverulent carrier such as lactose, saccharose, sorbitol, mannitol, starch (as e.g. potato starch, corn starch or amylopectin), cellulose derivatives or gelatin.

Dosage units for rectal dministration may be prepared in the form of suppositories, which contain the active substance in a mixture with a neutral fat base, or they may be prepared in the form of gelatin-rectal capsules which contain the active substance in a mixture with a vegetable oil or paraffin oil.

Liquid preparations for oral administration may be present in the form of syrups or suspensions, e.g. solutions containing from about 0.2% by weight to about 20% by weight of the active substance described, whereby the residue consists of sugar and a mixture of ethanol, water, glycerol and propylene glycol. If desired, such liquid preparations may contain coloring agents, flavoring agents, saccharine and carboxymethyl cellulose as a thickening agent.

Solutions for parenteral administration by injection may be prepared as an aqueous solution of a water-soluble pharmaceutically acceptable salt of the active compound, preferably in a concentration from about 0.5% by weight to about 10% by weight. These solutions may also contain stabilizing agents and/or buffering agents and may suitably be available in different dosage unit ampoules.

The preparation of pharmaceutical tablets for peroral use is carried out in accordance with the following method:

The solid substances included are ground or sieved to the particle size desired. The binding agent is homogenized and suspended in the desired amount of solvent. The therapeutic compound and necessary auxiliary agents are mixed while constantly mixing with the binding agent solution, and are moistened so that the solution is uniformly divided in the mass without overmoistening any parts. The amount of solvent is usually so adapted that the mass obtains a consistency similar to wet snow. The moistening of the pulverulent mixture with the binding agent solution causes the particles to gather together slightly into aggregates and the actual granulating process is carried out by pressing the mass through a sieve in the form of a net of stainless steel having a mesh size of about 1 mm. The mass is then placed in thin layers on a tray to be dried in a drying cabinet. This drying takes place during 10 hours and has to be standardized carefully as the moisture content of the granulate is of utmost importance for the ensuring process and for the characteristics of the tablets. Drying in a fluid bed may be used. In this case the mass is not put on a tray but is poured into a container having a porous bottom.

After the drying step the granules are sieved so that the desired particle size is obtained. Under certain circumstances powder has to be removed.

To the so-called final mixture, disintegrating, lubricating and anti-adhesive agents are added. After this mixing the mass has its correct composition for the tabletting step.

The tablet punching machine after cleaning is provided with a certain set of punches and dies, whereupon adjustment for the weight of the tablets and the degree of compression is made and tested. The weight of the tablet determines the size of the dose in each tablet and is calculated starting from the amount of therapeutic agent in the granules. The degree of compression affects the size of the tablet, its strength and its ability to disintegrate in water. Especially as regards the two later properties the choice of compression pressure (0.5 to 5 ton) requires balancing the conditions. When the correct adjustment is made, the preparation of tablets is started, which is carried out at a rate of 20,000 to 200,000 tablets per hour. The pressing of the tablets requires different times and depends on the size of the batch.

The tablets are freed from adhering powder in an apparatus designed for that purpose and are then stored in closed packages until they are delivered.

Many tablets, especially those which are rough or bitter, are coated with a layer of sugar or some other suitable material.

The tablets are usually packed by machines having an electronic counting device. The different types of packages include glass or plastic gallipots, and also boxes, tubes and specific dosage adapted packages.

The daily dose of the active substance varies and depends on the type of administration, but as a general rule it is 100 to 400 mg/day of active substance for peroral administration, and 5 to 20 mg per day at intravenous administration.

The following illustrates the principle and application of the invention, without however, being limited thereto. Temperature is given in degrees centigrade.

EXAMPLE 1

1,2-Epoxy-3-[4-(2-methylcarbamoyloxyethoxy)-phenoxy]-propane (13.1 g) was mixed with 100 ml of isopropanol and 13 ml of isopropylamine. The mixture is then heated on a boiling waterbath for 3 hours under reflux. Thereupon the reaction mixture is evaporated to dryness and the residue is dissolved in ether and the hydrochloride percipitates upon addition of gaseous HCl in either at pH 4. After recrystallization from acetonitrile the hydrochloride of 1-isopropylamino-3-[4-(2-methylcarbamoyloxyethoxy)-phenoxy]-propanol-2 is obtained. Melting point 124° C. Equ. weight: found 365, calcul. 362.5.

In accordance with the method of Example 1 the following compounds are obtained as hydrochlorides.

EXAMPLE 2

1-Isopropylamino-3-[2-chloro-4-(2-dimethylcarbamoyloxyethoxy)-phenoxy]-propanol-2. Melting point 115° C. Equ. weight: found 415, calculated 411.

EXAMPLE 3

1-Isopropylamino-3-[4-(2-carbamoyloxyethoxy)-phenoxy]-propanol-2. Melting point 146° C. Equ. weight: found 356, calculated 348.5.

EXAMPLE 4

1-Isopropylamino-3-[-(3-methylcarbamoyloxypropyl)-phenoxy]-propanol-2. Melting point 127.5° C. Equ. weight: found 361, calculated 360.5.

EXAMPLE 5

1-Isopropylamino-3-[4-(2-methylcarbamoyloxyethyl)-phenoxy]-propanol-2. Melting point 50° C. Equ. weight: found 349.5, calculated 346.5.

EXAMPLE 6

1-Isopropylamino-3-[2-chloro-4-(2-methylcarbamoyloxyethyl)-phenoxy]-propanol-2, was prepared from 2-chloro-4-(2-methylcarbamoyloxyethyl)-phenylglycidylether. M.p. 138° C.

EXAMPLE 7

1-Isopropylamino-3-/4-(2-dimethylcarbamoyloxyethyl)-phenoxy]-propanol-2 was prepared from 4-(2-dimethylcarbamoyloxyethyl)-phenylglycidylether. M.p. 115⁶ C.

EXAMPLE 8

1-Isopropylamino-3-[4-(2-carbamoyloxyethyl)-phenoxy]-propanol-2 was prepared from 4-(2-carbamoyloxyethyl)-phenylglycidylether. M.p. 108° C.

EXAMPLE 9 (Method A)

13 g of 2-chloro-4-(2-dimethylcarbamoyloxyethoxy)-phenol were added to 200 ml of epichlorohydrine and 0.5 ml of piperidine and the resulting mixture was heated on a boiling water bath for 10 hours. Thereupon the excess of epichlorohydrin was evaporated and the residue was dissolved in chloroform and was skaken first with 2N HCl and thereupon with $H_2O$. After evaporation the residue was dissolved in 50 ml of isopropanol and to the mixture 50 ml of isopropylamine was added and the resulting mixture was refluxed for 10 hours. The solvents were evaporated and to the residue 2N NaOH was added whereupon the mixture was extracted with ether. The ether phase was evaporated, whereupon the residues was transformed into its hydrochloride according to Example 1. In this way the hydrochloride of 1-isopropylamino-3-[2-chloro-4-(2-dimethylcarbamoyloxyethoxy)-phenoxy]-propanol-2 was obtained. M.p. 115° C. Equ. weight: found 412, calculated 411.

EXAMPLE 10 (Method B)

4-(2-Methylcarbamoyloxyethyl)-phenylglycidylether (10 g) in 100 ml of ethanol was saturated with gaseous ammonia and the mixture was heated in an autoclave on a boiling water bath for 4 hours. The mixture was evaporated and the residue was dissolved in ethyl acetate and gaseous HCl was introduced into the solution. Thereby the hydrochloride precipitated, and it was filtered off and dissolved in 60 ml of ethanol. To the ethanol solution 20 ml of isopropyliodide and 15 mg of $K_2CO_3$ were added. The mixture was heated in an autoclave at 120° C for 10 hours, whereupon it was evaporated and the residue was dissolved in 100 ml of 2N HCl and 100 ml of ether. The aqueous phase was separated off and was made alkaline with 2NNaOH and was extracted with ethyl acetate. The ethyl acetate phase was dried over $K_2CO_3$, whereupon the hydrochloride was precipitated with gaseous HCl. In this way the hydrochloride 1-isopropylamino-3-[4-(2-methylcarbamoyloxyethyl)-phenoxy]-propanol-2 was obtained. M.p. 51° C. Equ. weight: found 350, calculated 346.5.

EXAMPLE 11 (Method C)

2.4 g of Na were dissolved in 100 ml of ethanol whereupon 19.5 g of 4-(2-methylcarbamoyloxyethyl)-phenol and 15.2 g of 1-isopropylamino-3-chloropropanol-2 were added. The mixture was heated in an autoclave on a boiling water bath for 15 hours. Thereupon it was filtered and the filtrate was evaporated to dryness. The residue was made acidic with 2N HCl and was extracted with ether, whereupon it was made alkaline with NaOH and extracted with ether again. After drying of the ether phase over $K_2CO_3$ the hydrochloride was precipitated with gaseous HCl. In this way the hydrochloride of 1-isopropylamino-3-[4-(2-methylcarbamoyloxyethyl)-phenoxy]-propanol-2 was obtained. M.p. 50° C. Equ. weight: found 345, calculated 346.5.

EXAMPLE 12 (Method D)

In accordance with the foregoing example N-benzyl-1-isopropylamino-3-[4-(2-methylcarbamoyloxyethyl)-phenoxy]-propanol-2 hydrochloride was prepared from 4-(2-methylcarbamoyloxyethyl)-phenol and N-benzyl-1-isopropylamino-3-chloropropanol-2. 10 g of the compound thus obtained were dissolved in 100 ml of ethanol, were mixed with 0.5 g of Pd/C and were hydrogenated until the calculated amount of $H_2$ had been absorbed. After filtration the reaction mixture was evaporated to dryness and the residue was recrystallized from acetonitrile. The compound obtained, 1-isopropylamino-3-[4-(2-methylcarbamoyloxyethyl)-phenoxy]=propanol-2 hydrochloride, melted at 52° C. Equ. weight: found 348, calculated 346.5.

EXAMPLE 13 (Method E)

10 g of 1-Amino-3-[4-(2-methylcarbamoyloxyethyl)-phenoxy]-propanol-2 (obtained in accordance with method B above) were dissolved in 80 ml of methanol and 20 ml of acetone. The solution was cooled on an ice bath whereupon 10 g of sodium borohydride were added little by little. The temperature was then allowed to rise to ambient temperature and after 1 hour 200 ml of water was added and the resulting mixture was extracted with ether. The ether phase was dried over $K_2CO_3$ and the product was transformed into its hydrochloride. The hydrochloride of 1-isopropylamino-3-[4-(2-methylcarbamoyloxyethyl)-phenoxy]-propanol-2 obtained was recrystallized from acetonitrile. M.p. 51° C. Equ. weight: found 348, calculated 346.5.

EXAMPLE 14 (Method F)

1-Isopropylamino-3-[4-(2-aminoethyl)-phenoxy]-propanol-2. HCl (13 g) and potassium isocyanate (3.2 g) were dissolved in 50 ml of $H_2O$ and pH was adjusted to 5. The reaction mixture was heated under reflux overnight. Thereupon the reaction mixture was made alkaline by means of NaOH, whereupon an oil separated off. This oil was chromatographed on a silica acid column using ethanol as eluating agent. After evaporation the substance was dissolved in acetonitrile and mixed with a solution of m-hydroxybenzoic acid in ethanol. In this way the m-hydroxybenzoate of 1-isopropylamino-3-[4-(2-carbamoylaminoethyl)-phenoxy]-propanol-2 was obtained, which after recrystallization from isopropanol had a melting point of 138° C. Equ. weight: found 439.0, calculated 433.0.

EXAMPLE 15

1-Isopropylamino-3-[4-(2-aminoethyl)-phenoxy]-propanol-2 (7.3 g) was dissolved in 150 ml of methylenechloride and mixed with dimethylcarbamoyl chloride (1.65 g). The mixture was allowed to stand for 2 hours at room temperature, whereupon it was heated under reflux for 1 hour and then was filtered. The filtrate was evaporated, whereupon an oil was obtained which was chromatographed on silica gel using ethanol as eluating agent. When the ethanol had been evaporated a crystalline residue was obtained which was dissolved in ethanol-nitromethane and was mixed with a solution of gaseous HCl in ethyl acetate to pH 5. Thereby the hydrochloride of 1-isopropylamino-3-[4-(2-dimethylcarbamoylaminoethyl)-phenoxy]-propanol-2 was obtained in crystalline form from acetonitrile-nitromethane. The melting point was 152° C. Equ. weight: found 366.0, calculated 359.9.

The following compounds were obtained according to the method described in Example 14.

EXAMPLE 16

1-Isopropylamino-3-[2-chloro-4-(2-carbamoylaminoethyl)-phenoxy]-propanol-2 was prepared from 1-isopropylamino-3-[2-chloro-4-(2-aminoethyl)-phenoxy]-propanol-2. M.p. 117° C.

EXAMPLE 17

1-Isopropylamino-3-[4-(3-carbamoylaminopropyl)-phenoxy]-propanol-2 was prepared from 1-isopropylamino-3-[4-(3-aminopropyl)-phenoxy]-propanol-2. M.p. 110° C.

EXAMPLE 18

1-Isopropylamino-3-[4-(2-methylcarbamoylaminoethyl)-phenoxy]-propanol-2 was prepared from 1-isopropylamino-3-[4-(2-aminoethyl)-phenoxy]-propanol-2. M.p. 118° C.

EXAMPLE 19

A syrup containing 2% (weight per volume) of active substance was prepared from the following ingredients:

1-Isopropylamino-3-[4-(2-methylcarbamoyloxyethoxy)-phenoxy]-propanol-2. HCl: 2.0 g
Saccharine: 0.6 g
Sugar: 30.0 g
Glycerine: 5.0 g
Flavoring agent: 0.1 g
Ethanol 96%: 10.0 ml
Distilled water: ad 100.0 ml.

Sugar, saccharine and the ether salt were dissolved in 60 g of warm water. After cooling glycerine and a solution of flavoring agents dissolved in ethanol were added. To the mixture, water was then added to 100 ml.

21

The above mentioned active substance may be replaced with other pharmaceutically acceptable acid addition salts.

EXAMPLE 20

1-Isopropylamino-3-[2'-chloro-4'-(2-dimethylcarbamoyloxyethoxy)-phenoxy]-propanol-2-hydrochloride (250 g) was mixed with lactose (175.8 g), potato starch (169.7 g) and colloidal silicic acid (32 g). The mixture was moistened with a 10% solution of gelatin and was granulated through a 12 mesh sieve. After drying, potato starch (160 g), talc (50 g) and magnesium stearate (5 g) were admixed and the mixture thus obtained was pressed into tablets (10,000) which contain 25 mg of substance. The tablets are sold on the market provided with a breaking score to give fractional or multiple doses when broken.

EXAMPLE 21

Granules were prepared from 1-isopropylamino-3-[4-(2-carbamoyloxyethoxy)-phenoxy]-propanol-2-hydrochloride (250 g), lactose (175.9 g) and an alcoholic solution of polyvinylpyrrolidone (25 g). After the drying step the granules were mixed with talc (25 g), potato starch (40 g) and magnesium stearate (2.50 g) and pressed into 10,000 biconvex tablets. These tablets are primarily coated with a 10% alcoholic solution of shellac and thereafter with an aqueous solution containing saccharose (45%), gum arabic (5%), gelatin (4%) and dyestuff (0.2%). Talc and powdered sugar were used for powdering after the first five coatings. The coating was then coated with a 66% sugar syrup and polished with a 10% carnauba wax solution in carbon tetrachloride.

EXAMPLE 22

1-Isopropylamino-3-[4-(2-dimethylcarbamoylaminoethyl)-phenoxy]-propanol-2-hydrochloride (1 g), sodium chloride (0.8 g) and ascorbic acid (0.1 g) were dissolved in a sufficient amount of distilled water to give 100 ml of solution. This solution, which contains 10 mg of active substance on each ml, was used in filling ampoules, which were sterilized by heating at 120° C for 20 minutes.

PHARMACOLOGICAL EVALUATION

The compounds prepared according to examples 1-18 were evaluated for intrinsic activity and blocking effect on heart rate and for peripheral vasodilator response to isoprenaline in the cat. Alprenolol was used as a reference substance.

Cats weighing between 1.8 kg were anaesthetized with 30 mg/kg pentobarbital sodium i.p. The cats had been pretreated with reserpine, 5 mg/kg i.m. about 18 hours before the experiment. Bilateral vagotomy was performed before the start of the experiment.

The heart rate was recorded on an Offner cardiotachometer triggered by the EKG-complex. Mean intraarterial blood pressure was recorded from a carotid artery. The peripheral resistance was measured in one of the legs of the cat in the following way: The femoral artery was opened in the inguinal region and the leg was perfused by blood delivered through a sigma motor pump at constant rate. The flow resistance (the pressure) was recorded via a strain gauge transducer connected to the catheter distally to the pump. The paw was excluded from the circulation by a tight ligature around the ankle. Intravenously injected isoprenaline increased the heart rate and reduced the perfusion pressure. An isoprenaline dose giving 70–80% of the maximal chronotropic response was determined. This dose (usually 0.1 µg/kg) was then repeated with 20 minute intervals. Ten minutes before each isoprenaline injection, the tested substances were administered intravenously for two minutes, starting with a dose of 0.01 mg/kg and increasing each subsequent dose fourfold. The intrinsic effects of the test substances were determined. The dose producing 50% blockade of the isoprenaline responses were evaluated from the plotted log dose-percent blockade diagrams.

TABLE

Intrinsic stimulating activity on heart rate in cats, beta-blocking activity on heart rate and peripheral vascular resistance in cat;

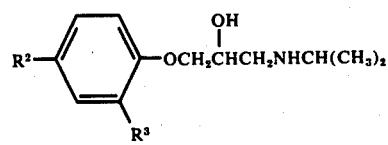

| Compound R² | R³ | Reserpinized cat Intrinsic activity % of isoprenaline heart rate response | β-blockade Heart rate ED$_{50}$ mg/kg | β-blockade Peripheral vascular resistance ED$_{50}$ mg/kg |
|---|---|---|---|---|
| o-allyl (alprenolol) | | 20 | 0.1 | 0.05 |
| CH$_3$NHCO—OC$_2$H$_4$O— | H | 25 | 0.5 | >8.5 |
| (CH$_3$)$_2$NCO—O—C$_2$H$_4$O— | Cl | 5 | 0.1 | 1.7 |
| H$_2$NCO—O—C$_2$H$_5$O— | H | 40 | 0.4 | 8 |
| CH$_3$NHCO—O—C$_2$H$_4$— | H | 0 | 0.4 | 2.4 |
| CH$_3$NHCO—O—C$_2$H$_4$— | Cl | 0 | 0.3 | 1.8 |
| H$_2$NCONHC$_2$H$_4$— | H | 0 | 0.4 | 14 |
| H$_2$NCONHC$_2$H$_4$— | Cl | 0 | 0.4 | 2.6 |

As is evident from the Table, the seven test substances were 1 to 5 times less active than alprenolol as regards blockade of the β-receptors of the heart. However, the peripheral vascular β-blocking activity for the seven test substances was 34–280 times lower than the activity of alprenolol.

The results demonstrate that the seven test substances developed a relatively stronger blockade of the β-receptors of the heart than of the receptors in smooth muscles. Due to its cardioselectivity, the test sub-

We claim:
1. An amine of the formula I

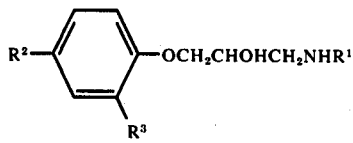

wherein R¹ is lower alkyl or hydroxy lower alkyl, R² is carbamoylamino lower alkyl, mono lower alkyl carbamoylamino lower alkyl, di-lower alkyl carbamoylamino lower alkyl, carbamoylamino lower alkoxy, mono lower alkyl carbamoylamino lower alkoxy, di-lower alkyl carbamoylamino lower alkoxy, and R³ is hydrogen, halogen, lower alkyl, lower alkenyl, lower alkinyl, lower alkoxymethyl, lower alkoxy, lower alkenyloxy, lower alkinyloxy, lower alkylthio, lower alkenylthio, lower alkinylthio or lower acyl; or an addition salt of said compound I with a pharmaceutically acceptable non-toxic acid.

2. A compound according to claim 1 of the formula Ic

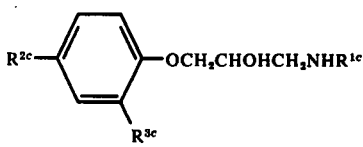

wherein R¹$^c$ is lower alkyl having 1 to 4 carbon atoms or hydroxy lower alkyl having 1 to 4 carbon atoms, R²$^c$ is lower alkyl carbamoylamino lower alkyl having up to 10 carbon atoms and R³$^c$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, or lower alkenyloxy having 3 or 4 carbon atoms.

3. An amine of the formula Ic according to claim 2, wherein R¹$^c$ is tert.-butyl, isopropyl, 1-hydroxypropyl-2 or 1-hydroxy-2-methylpropyl-2, R²$^c$ is methylcarbamoylamino methyl, methylcarbamoylamino ethyl, methylcarbamoylamino-n-propyl or di-methylcarbamoylamino ethyl and R³$^c$ is hydrogen, chloro, bromo, methyl, allyl, methoxymethyl, methoxy or allyloxy.

4. An amine of the formula Ic according to claim 2, wherein R¹$^c$ is tert.-butyl or isopropyl, R²$^c$ is di-methyl carbamoylamino ethyl or methyl carbamoylamino ethyl and R³$^c$ is hydrogen, chloro, bromo, allyl, methyl, methoxymethyl, methoxy or allyloxy.

5. A compound according to claim 1 of the formula Id

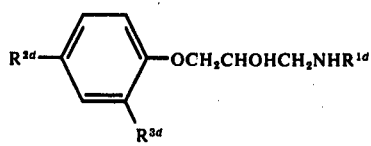

wherein R¹$^d$ is lower alkyl having 1 to 4 carbon atoms or hydroxy lower alkyl having 1 to 4 carbon atoms, R²$^d$ is carbamoylamino lower alkyl having up to 5 carbon atoms and R³$^d$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms, or lower alkenyloxy having 3 or 4 carbon atoms.

6. An amine of the formula Id according to claim 5, wherein R¹$^d$ is tert.-butyl, isopropyl, 1-hydroxypropyl-2 or 1-hydroxy-2-methylpropyl-2, R²$^d$ is carbamoylaminomethyl, carbamoylaminoethyl, carbamoylamino-n-propyl or carbamoylamino-n-butyl and R³$^d$ is hydrogen, chloro, bromo, methyl, allyl, methoxymethyl or methoxy.

7. An amine of the formula Id according to claim 5, wherein R¹$^d$ is tert.-butyl or isopropyl, R²$^d$ is carbamoylamino lower alkyl and R³$^d$ is chloro, bromo, allyl, methyl, methoxymethyl, methoxy or allyloxy.

8. An amine of the formula Ig

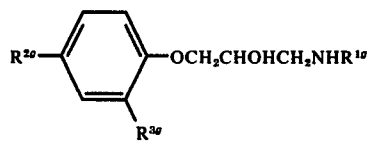

wherein R¹$^g$ is lower alkyl having 1 to 4 carbon atoms or hydroxy lower alkyl having 1 to 4 carbon atoms, R²$^g$ is carbamoylamino lower alkoxy having up to 5 carbon atoms and R³$^g$ is hydrogen, halogen, lower alkyl having 1 to 4 carbon atoms, lower alkenyl having 2 to 4 carbon atoms, lower alkoxy methyl having up to 5 carbon atoms, lower alkoxy having 1 to 4 carbon atoms or lower alkenyloxy having 3 or 4 carbon atoms.

9. An amine of the formula Ig according to claim 8, wherein R¹$^g$ is tert.-butyl, isopropyl, 1-hydroxypropyl-2 or 1-hydroxy-2-methylpropyl-2, R²$^g$ is carbamoylaminomethoxy, carbamoylaminoethyoxy or carbamoylamino-n-propoxy and R³$^g$ is hydrogen, chloro, bromo, methyl, allyl, methoxymethyl, methoxy or allyloxy.

10. An amine of the formula Ig according to claim 8, wherein R¹$^g$ is tert.-butyl or isopropyl, R²$^g$ is carbamoylamino ethoxy and R³$^g$ is hydrogen, chloro, bromo, allyl, methyl, methoxymethyl, methoxy or allyloxy.

11. A compound according to claim 1 in the form of its dextro-rotating optical antipode.

12. A compound according to claim 1 in the form of its levo-rotating optical antipode.

13. A compound according to claim 1 in its free base form.

14. A compound according to claim 1 in the form of an addition salt with a pharmaceutically acceptable non-toxic acid.

15. A compound according to claim 1 selected from the group consisting of
1-[4-(2-carbamoylaminoethyl)-phenoxy]-2-hydroxy-3-isopropylaminopropane,
1-[4-(2-dimethylcarbamoylaminoethyl)-phenoxy]-2-hydroxy-3-isopropylaminopropane,
1-[2-chloro-4-(2-carbamoylaminoethyl)-phenoxy]-2-hydroxy-3-iropropylaminopropane,
1-[4-(3-carbamoylaminopropyl)-phenoxy]-2-hydroxy-3-isopropylaminopropane, or
1-[4-(2-methylcarbamoylaminoethyl)-phenoxy]-2-hydroxy-3-isopropylaminopropane.

* * * * *

UNITED STATES PATENT AND TRADEMARK OFFICE
CERTIFICATE OF CORRECTION

PATENT NO. : 4,035,420
DATED : July 12, 1977
INVENTOR(S) : Peder Bernhard Berntsson et al.

It is certified that error appears in the above-identified patent and that said Letters Patent are hereby corrected as shown below:

Claim 9, column 24, line 37, "carbamoylaminoethyoxy" should be -- carbamoylaminoethoxy --.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks